(12) United States Patent
Sommer

(10) Patent No.: US 7,741,623 B2
(45) Date of Patent: Jun. 22, 2010

(54) PATIENT POSITIONING DEVICE

(75) Inventor: Andres Sommer, Langensendelbach (DE)

(73) Assignee: Siemens Aktiengesellschaft, Munich (DE)

(*) Notice: Subject to any disclaimer, the term of this patent is extended or adjusted under 35 U.S.C. 154(b) by 163 days.

(21) Appl. No.: 12/064,787

(22) PCT Filed: Aug. 25, 2006

(86) PCT No.: PCT/EP2006/065674

§ 371 (c)(1),
(2), (4) Date: Feb. 25, 2008

(87) PCT Pub. No.: WO2007/025936

PCT Pub. Date: Mar. 8, 2007

(65) Prior Publication Data

US 2008/0234865 A1 Sep. 25, 2008

(30) Foreign Application Priority Data

Sep. 1, 2005 (DE) ............ 10 2005 041 606

(51) Int. Cl.
*A61N 5/00* (2006.01)
*G21G 5/00* (2006.01)

(52) U.S. Cl. ............... 250/492.3; 250/492.1; 250/493.1; 250/503.1; 250/522.1; 5/601; 5/607; 5/610; 5/611; 378/64; 378/65; 378/178; 378/209

(58) Field of Classification Search ............... 250/492.3, 250/492.1, 493.1, 503.1, 522.1; 5/601, 607, 5/610, 611; 378/64, 65, 178, 209
See application file for complete search history.

(56) References Cited

U.S. PATENT DOCUMENTS 3,627,250 A 12/1971 Pegrum (Continued)

FOREIGN PATENT DOCUMENTS

DE 90 12 435 U1 1/1992

(Continued)

OTHER PUBLICATIONS

Katuin, J.E., et al., "The Use of Industrial Robot Arms for High Precision Patient Positioning" AIP Conference Proceedings, vol. 680, No. 1, Aug. 26, 2003, pp. 1138-1141, XP002404457 17. International conference on the application of accelerators in research and industry, Denton, TX.

(Continued)

*Primary Examiner*—Jack I Berman
*Assistant Examiner*—Meenakshi S Sahu
(74) *Attorney, Agent, or Firm*—Brinks, Hofer, Gilson & Lione

(57) ABSTRACT

The invention relates to a patient-positioning device for positioning a patient in an irradiation position in a radiation therapy arrangement, in particular in a particle radiation therapy arrangement comprising a patient supporting module, which is provided with a patient supporting device for holding the patient in a body holder where the irradiation is to be carried out, wherein, said patient supporting device is mounted on a base unit in such a way that it is rotatable about an axis by means of a bearing, said base unit is provided with a coupling element, the inventive device is also provided with a positioning arm, which comprises several joints and a coupling point for coupling the coupling element and for freely positioning the patient in any predefined irradiation position by adjusting the angle of rotation of the patient supporting module.

12 Claims, 2 Drawing Sheets

U.S. PATENT DOCUMENTS

| | | |
|---|---|---|
| 4,705,955 A | 11/1987 | Mileikowsky |
| 2005/0114996 A1* | 6/2005 | Somasundaram ............. 5/601 |

FOREIGN PATENT DOCUMENTS

| | | |
|---|---|---|
| DE | 10 2004 013 174 A1 | 10/2005 |
| DE | 10 2004 032 012 A1 | 1/2006 |
| DE | 10 2004 032012 A1 | 1/2006 |
| EP | 0 283 083 A | 9/1988 |
| EP | 0 490 107 A1 | 6/1992 |
| EP | 0 860 145 A1 | 8/1998 |
| EP | 1 283 734 A0 | 2/2003 |
| EP | 1 323 503 A2 | 7/2003 |
| FR | 2 836 468 A1 | 8/2003 |
| JP | 8-266650 | 10/1996 |
| WO | WO 2005/018735 A2 | 3/2005 |
| WO | WO 2005/099819 A2 | 10/2005 |

OTHER PUBLICATIONS

PCT International Search Report dated Nov. 17, 2006.
PCT Written Opinion and English translation dated Nov. 17, 2006.
German Office Action dated May 5, 2006 with English translation for corresponding German Patent Application No. DE 10 2005 041 606.3-54.
Katuin, J.E., et al., "The Use of Industrial Robot Arms for High Precision Patient Positioning," *AIP Conference Proceedings*, vol. 680, No. 1, Aug. 26, 2003, pp. 1138-1141, XP002404457 17, International Conference on the Application of Accelerators in Research and Industry, Denton, Texas.
Mazal, A., et al., "*La Protonthérapie: Bases Physiques et Technologiques*," Bull Cancer/Radiother 1996:83, pp. 230-246, Elsevier, Paris, 1996.
Meggiolaro, Marco A., "*Geometric and Elastic Error Calibration of a High Accuracy Patient Positioning System*," Mechanism and Machine Theory 40 (2005), pp. 415-427, 2005.

* cited by examiner

PATIENT POSITIONING DEVICE

The present patent document is a 35 U.S.C. §371 application of PCT Application Serial Number PCT/EP2006/065674, filed Aug. 25, 2006, designating the United States, which is hereby incorporated by reference. This patent document also claims the benefit of German patent application DE 10 2005 041 606.3, filed Sep. 1, 2005, which is hereby incorporated by reference.

BACKGROUND

The present embodiments relate to a patient positioning device for positioning a patient in an irradiation position for a radiation therapy system, in particular a particle beam therapy system.

In radiation therapy, it is of particular importance to be able to position the patient with high precision in an irradiation position for the radiation treatment. To enable selecting the angle of incidence of the radiation as freely as possible in planning the therapy, a patient positioning device should assure the applicable freedoms for orienting the patient in his posture for the radiation treatment.

From European Patent Disclosure EP 1 283 734 B1, a device for placing a tumor patient, with a tumor in the head or neck area, in a heavy-ion therapy chamber is known. The device has a patient chair, on which a patient can be fixed in a seated posture and which can be moved translationally as well as rotated about a horizontal axis and a vertical axis. The device is fixedly mounted and thus fixedly associated with a treatment site.

SUMMARY AND DESCRIPTION

A patient positioning device may be used flexibly and assure freedom in orienting the patient relative to a treatment beam.

One embodiment of the patient positioning device, for example, includes a patient supporting module with a patient supporting device for keeping the patient in a posture intended in the radiation treatment planning. The patient supporting device is mounted rotatably about an axis above a bearing at a base unit of the patient supporting module. The base unit has a coupling element, with which the patient supporting module can be coupled to a device having a positioning arm. The positioning arm of the patient positioning device has a plurality of joints and a coupling point for coupling the coupling element of the patient supporting module. The rotary motion of the patient supporting device and the free mobility of the positioning arm allow free positioning of the patient in an arbitrarily predeterminable irradiation position.

A therapy chair, for example, can also be held with the aid of a robotic drive. Because of the geometry of the patient and the usual robot mechanism, for instance, it is not readily possible for a robot drive to dock with the therapy chair from below. For this reason, the coupling element is preferably located laterally on the base element.

The patient can be rotated 360° in any orientation of the positioning arm.

In a further embodiment, the patient supporting device is embodied as a gurney (bed) or patient chair. The patient supporting device may include a motor for driving the support annularly, for rotation by 360°, or another angular segment.

The positioning arm may be embodied as a robot arm, which has free mobility about a plurality of joints about a plurality of axes.

In one embodiment, the patient supporting module has a mechanical shield for protecting the extremities or for monitoring the motion with regard to possible contacts with external objects. This is accomplished for instance via pressure sensors or infrared distance measurement. The shield may completely surround the area to be protected.

Further advantageous embodiments are defined by the subjects of the dependent claims.

DETAILED DESCRIPTION

Figure 1:
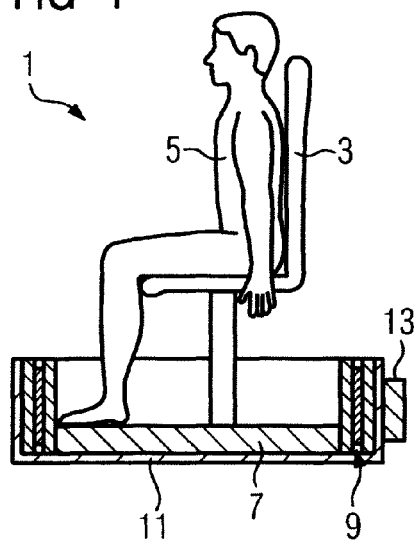
FIG. 1 shows a cross section through an example of a patient supporting module.

FIG. 1 shows an example patient supporting module 1 with a patient chair 3 as a patient supporting device. A patient 5 sits on the patient supporting device, preferably fixed, in a radiation treatment posture. The patient chair 3 is secured to a base plate 7 and can be rotated by a bearing 9. The rotation may be by 360°. The bearing 9 is fixedly connected to a base plate 11. The base plate 11 is U-shaped in cross section. A coupling element 13 is disposed on the radial outside of the base plate 11.

Figure 2:
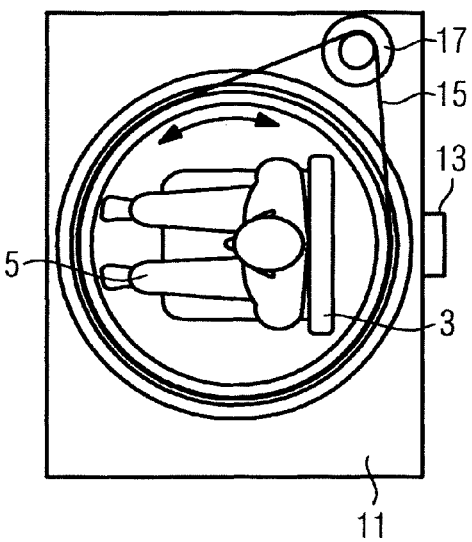
FIG. 2 shows a plan view on an example of a patient positioning module driven by a motor.

FIG. 2 shows a plan view of an exemplary embodiment of a patient supporting module similar to the patient supporting module 1 of FIG. 1. For the sake of clarity, a belt drive is also shown. The belt drive has a belt 15 and a drive motor 17.

Figure 3:
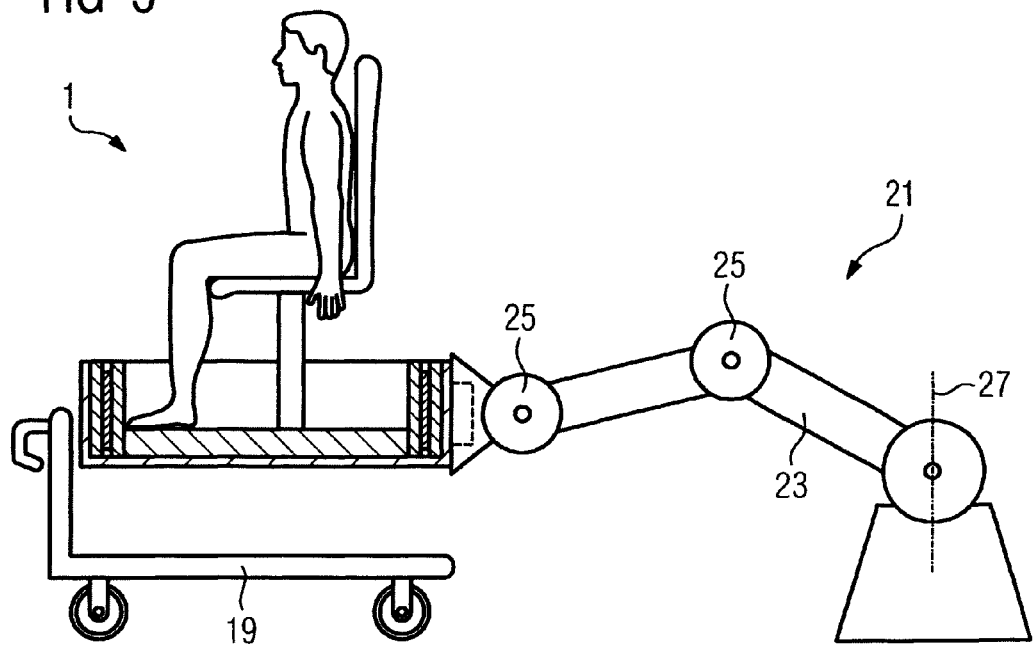
FIGS. 3 and 4 illustrate the use of an example of a patient positioning device.
Figure 4:
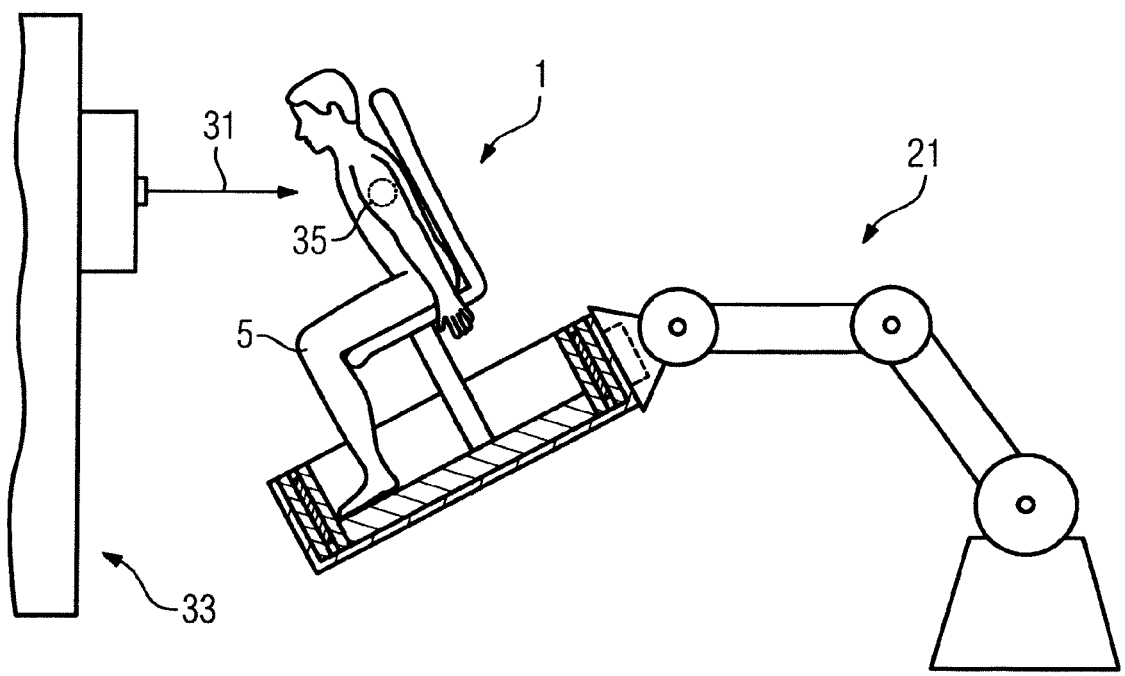

FIGS. 3 and 4 illustrate the use of an example patient positioning device. A patient is prepared for the radiation treatment on the patient supporting module 1. The patient assumes a posture on which the radiation treatment planning was based, for instance by being put into the appropriate position with the aid of a fixation device.

With the aid of a transporting device 19, the patient chair is brought from a preparation room or space to a device 21 with a positioning arm 23. There, a coupling point of the positioning arm 23 is coupled with a coupling element of the patient supporting module 1. The positioning arm has a plurality of joints 25, which make free orientation of the positioning arm in space possible. The positioning arm is, for example, also pivotable about a vertical axis 27.

The patient positioning device is triggered from a treatment control center of a radiation therapy system. This makes it possible, as shown in FIG. 4, to orient the patient in such a way with respect to a treatment beam 31, such as a photon, electron, neutron, pion, proton, helium-ion, carbon-ion, or oxygen-ion beam. If the treatment beam 31, for example, belongs to a fixed-beam radiation treatment site 33, then the versatility of such a treatment site can be expanded substantially with the aid of the patient positioning device. The freedom in adjusting the angle of incidence leads to a wide range of adjustable angles of incidence of the treatment beam 31 with respect to an area 35 of the patient 5 that is to be treated.

If such a patient positioning device is combined with various patient supporting devices—for instance with a patient chair, a gurney, and so forth—then the flexibility in use of radiation treatment sites, especially fixed-beam radiation treatment sites, is increased still further.

Figure 5:
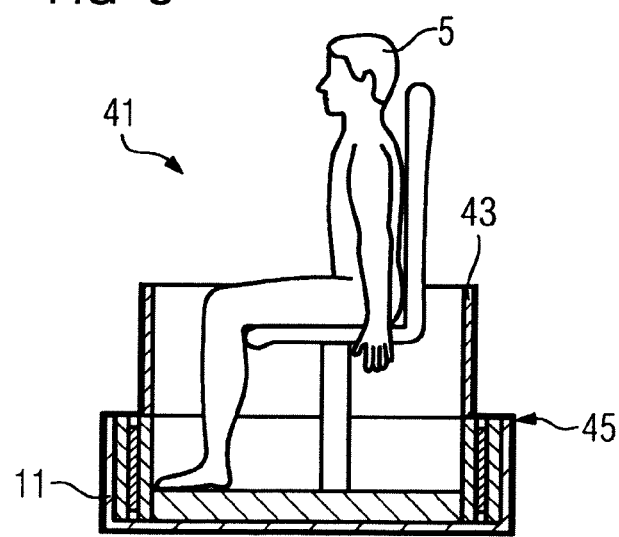
FIG. 5 shows an exemplary embodiment of a patient positioning module with a protection device and with a sensor system.

FIG. 5 shows a further embodiment of a patient positioning module 41. A shield 43 extends radially around the patient 5 in the area of his legs, and pressure sensor systems 45 are disposed both on the outside of the shield 43 and on the underside of the base plate 11. In this embodiment, the patient 5 is protected passively against unwanted actions from outside by way of the guard ring 43. The patient is protected against such actions by way of an interruption in the triggering of a positioning arm (not shown) upon activation of one of the pressure sensor systems 45.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A patient positioning system for positioning a patient in an irradiation position by a radiation therapy system, the patient positioning system comprising:
   a patient supporting module having:
      a patient supporting device, wherein the patient supporting device keeps the patient in a posture on which radiation treatment planning was based,
      a base unit having a coupling element, and
      a bearing that is connected to the base unit and operable to rotate the patient supporting device with respect to the base unit; and
   a positioning arm having a plurality of joints and a coupling point for coupling with the coupling element of the base unit,
   wherein the positioning arm provides positioning of the patient with adjustment of a rotary angle of the patient supporting module in the irradiation position.

2. The patient positioning system as defined by claim 1, wherein the patient supporting device is a gurney or patient chair.

3. The patient positioning system as defined by claim 1, wherein the patient supporting module has a motor for driving the bearing, the bearing being embodied annularly.

4. The patient positioning system as defined by claim 1, wherein the positioning arm is movable about a plurality of axes by the plurality of joints.

5. The patient positioning system as defined by claim 1, wherein the patient supporting module has a mechanical shield for protecting the extremities of the patient.

6. The patient positioning system as defined by claim 5, wherein the shield has at least one sensor, which upon activation trips stoppage of motion.

7. The patient positioning system as defined by claim 6, wherein the sensor is a pressure sensor, which is activated by a pressure exerted by of contact with an external object.

8. The patient positioning system of claim 1, wherein the positioning arm and plurality of joints comprise a robot arm.

9. The patient positioning system of claim 1, wherein the radiation therapy system comprises a particle beam therapy system.

10. The patient positioning system as defined by claim 2, wherein the patient supporting module has a motor for driving the bearing, the bearing being embodied annularly.

11. The patient positioning system as defined by claim 10, wherein the positioning arm is movable about a plurality of axes by the plurality of joints.

12. The patient positioning system as defined by claim 11, wherein the patient supporting module has a mechanical shield for protecting the extremities of the patient.

* * * * *